United States Patent [19]

Hiratani

[11] 4,433,151
[45] Feb. 21, 1984

[54] OXY BENZOIC ACID TERMINATED POLYETHER DERIVATIVES OF 8-HYDROXY QUINOLINES

[75] Inventor: Kazuhisa Hiratani, Ibaragi, Japan

[73] Assignee: Director-General of Agency of Industrial Science & Technology, Tokyo, Japan

[21] Appl. No.: 353,107

[22] Filed: Mar. 1, 1982

[30] Foreign Application Priority Data

Mar. 9, 1981 [JP]  Japan ................................. 56-34101

[51] Int. Cl.³ ................ C07D 215/24; C07D 215/26; C07D 215/30
[52] U.S. Cl. ........................................ 546/178; 423/2; 423/6; 423/24
[58] Field of Search ........................................ 546/178

[56] References Cited

U.S. PATENT DOCUMENTS 3,403,326  3/1976  Richman ..................... 260/239 BC
3,891,655  6/1975  Palmer ................................. 546/178

FOREIGN PATENT DOCUMENTS 56-128763  10/1981  Japan ................................. 546/178

Primary Examiner—Paul M. Coughlan, Jr.
Assistant Examiner—David B. Springer
Attorney, Agent, or Firm—Stephen F. K. Yee

[57] ABSTRACT

A novel polyether having the following general formula:

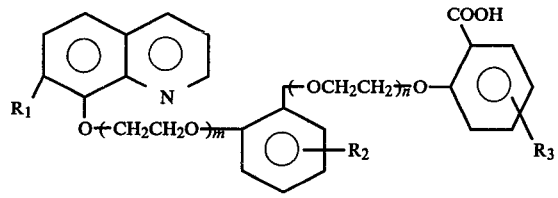

wherein $R_1$, $R_2$ and $R_3$ each stand for hydrogen, an alkyl group having 1 to 20 carbon atoms or an alkenyl group having 1 to 20 carbon atoms with the exception that $R_1$, $R_2$ and $R_3$ cannot stand for hydrogen at the same time, and m and n each represent an integer of 1 to 9. The polyether can capture cations when contacted with a cation-containing aqueous alkaline liquid and can release the cations to an aqueous acidic liquid, and thus serves as a cation carrier.

4 Claims, 1 Drawing Figure

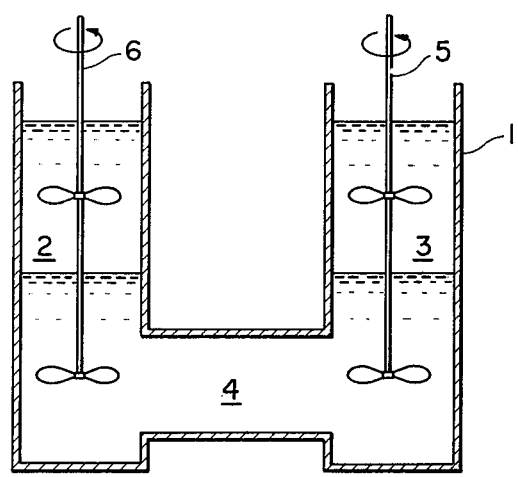

OXY BENZOIC ACID TERMINATED POLYETHER DERIVATIVES OF 8-HYDROXY QUINOLINES

DETAILED DESCRIPTION OF THE INVENTION

This invention relates to novel polyether derivatives useful as a carrier for transporting cations from one aqueous liquid to another aqueous liquid.

Concentration and extraction of cations such as metal ion become very important techniques in many fields such as biochemical and radiochemical arts.

It is an object of the present invention to provide a novel polyether derivative capable of capturing cations in a cation-containing liquid and of liberating the captured cations to another liquid. Another object of this invention is to provide a polyether of the above-mentioned type with which the transportation of cations can be done at a high rate. It is a further object of this invention to provide a polyether of the above-mentioned type which can selectively transport alkali metals.

In accomplishing the foregoing objects, there is provided in accordance with the present invention a polyether having the following general formula (I):

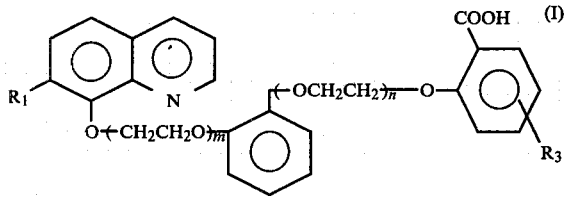

wherein $R_1$, $R_2$ and $R_3$ each stand for hydrogen, an alkyl group having 1 to 20 carbon atoms or an alkenyl group having 1 to 20 carbon atoms with the exception that $R_1$, $R_2$ and $R_3$ cannot stand for hydrogen at the same time, and m and n each represent an integer of 1 to 9.

In another aspect, the present invention provides a method of transporting cations in a first liquid to a second liquid, which comprises contacting a third liquid immiscible with said first and second liquids and containing the above polyether with said first liquid so that the cations in the first liquid may be captured by the polyether, and contacting the third liquid containing the cations captured by the polyether with the second liquid so that the cations may be released to the second liquid.

The polyether according to this invention, when subjected to a pH region of about 8 to 13, can be in the form of carboxylate ($COO^-$) and can capture cations. It is presumed that not only the carboxylate but also the oxygen atoms of the ether linkages of the polyether interact with the cation to embrace the cations in the polyether molecules. At a pH in the range of about 1 to 6, the polyether can exist in the form of carboxylic acid (COOH) and can liberate the captured cations.

Thus, the polyether can serve to act as a carrier for the transportation of cations. Illustrative of such cations are those of alkali metals, alkaline earth metals and heavy metals. Ammonium ion and organic cations such as certain amino acids may also be transported by the cation carrier of this invention. The polyether of this invention is particularly useful for transporting alkali metal ion.

The transportation of cations can be done by contacting a first, cation-containing liquid, generally an aqueous alkaline liquid preferably having a pH of about 8 to 13, with a third liquid, generally an organic solvent solution, containing the polyether of this invention and immiscible with the first liquid so that the cations may be captured by the polyether. Illustrative of the organic solvents are halogenated organic solvents such as chloroform, carbon tetrachloride and dichloroethane; hydrocarbons such as benzene, cyclohexane and n-hexane; and higher alcohols such as octanol and hexanol. The concentration of the polyether in the third liquid is generally in the range of $10^{-5}$ to $10^{-1}$ mol/l, preferably $10^{-3}$ to $10^{-2}$ mol/l. The third liquid thus containing the cations captured by the polyether is then contacted with a second liquid, generally an aqueous acidic liquid preferably having a pH of about 1 to 6, and immiscible with the third liquid so that the polyether changes into the form of carboxylic acid with the simultaneous liberation of the captured cations to the second liquid.

A preferred embodiment according to the present invention will now be described with reference to the accompanying drawing in which the sole FIGURE is an elevational, cross-sectional view diagrammatically showing an apparatus useful for performing the cation transportation using the polyether of this invention.

Referring to the FIGURE, designated by the reference numeral 1 is a U-shaped vessel equipped with stirrer means 5 and 6 in its respective vertical portions. The third, polyether-containing liquid is contained in the vessel 1 to form a third layer 4 with its liquid level positioned adjacent to the respective lower portions of the vertical portions. The first and second liquids are then poured into the vessel 1 to form first and second layers 2 and 3 on the third layer 4. In the interface at which the first and third layers 2 and 4 are contacted, the cations in the layer 2 are captured by the polyether contained in the layer 4, while in the interface at which the second and third layers 3 and 4 are contacted, the cations captured by the polyether are liberated and released to the second layer 3. The stirrer means 5 and 6 are continuously operated to facilitate the capture and the liberation of the cations. In this method, the third layer 4 should, of course, have a higher specific gravity than the other layers 2 and 3.

If desired, a suitable membrane may be disposed between the first and third liquids and between the second and third liquid. In a special case, the polyether may be supported on a suitable support means such as filter paper or high molecular weight membrane and each side of the polyether-supporting means is contacted with respective one of the first and the second liquids. The transportation may also be effected by usual extraction method in which the first and the third liquids are vigorously shaken together to extract the cation with the third liquid, the cation contained in the third liquid being subsequently extracted with the second liquid.

With the polyether according to this invention, the transportation of cations may be effected very fast. Further, even when the concentration of cations in the first liquid is lower than that in the second liquid, the polyether of this invention can carry the cations from the first to second liquids. The polyether of this invention has a further feature in that it exhibits preference for alkali metals in the presence of other metal ions. The order of the preference for alkali metals varies with the change in the length of ethyleneoxy chains of the polyether. In the case of a polyether of the above general formula (I) in which m is 2 and n is 2, for example, the preference increases in the order: Li<Na<Cs<<Rb<K. That is, when these alkali metals are contained in equal amounts in the first liquid, the polyether will selectively transport potassium ion.

The polyether of this invention may be prepared any known manner. For example, an ethylene glycol derivative of the general formula (II):

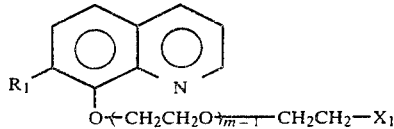

(II)

wherein $X_1$ is a halogen atom and $R_1$ and m have the same meaning as above, is reacted with a pyrocatechine derivative of the formula (III):

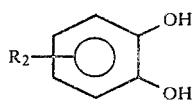

(III)

wherein $R_2$ has the same meaning as above, in an alkaline medium to form a compound of the formula (IV):

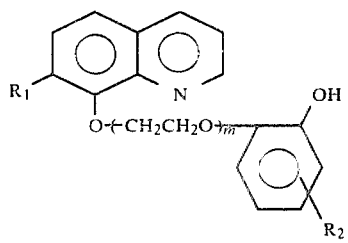

(IV)

The compound of the formula (IV) is then reacted with an ester of the formula (V):

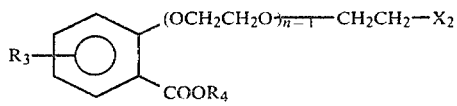

(V)

wherein $X_2$ is a halogen atom and $R_4$ is a lower alkyl group, in an alkaline medium to form an alkyl ester. The hydrolysis of the thus obtained ester gives the polyether of the formula (I). The reactions between the compound (II) and the compound (III) and between the compound (IV) and the compound (V) are carried out at a temperature of 30° to 150° C. in a suitable solvent such as dimethylformamide, hexamethylphosphoramide, dimethyl sulfoxide and n-butanol. Examples of alkaline substances suitable for the formation of the alkaline medium include sodium hydride, potassium carbonate, sodium hydroxide and potassium hydroxide.

The following examples will further illustrate the present invention.

EXAMPLE 1

To a mixture of 16.6 g (0.1 mol) of 4-t-butylcatechol and 1.2 g (0.05 mol) of sodium hydride in 100 ml of dimethylformamide were added 12.6 g (0.05 mol) of a quinoline derivative of the formula:

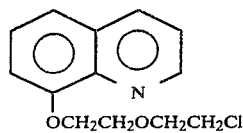

and the resulting mixture was allowed to react at a temperature of 70° C. for 6 days with stirring. After completion of the reaction, the reaction mixture was added with water. Solvent extraction was performed twice with chloroform and the chloroform layer was, after being washed with water, dried over magnesium sulfate. Thereafter, chloroform was distilled off and the residue was subjected to column chromatography, thereby to obtain 11.5 g of a product consisting of the following two compounds in equal proportion.

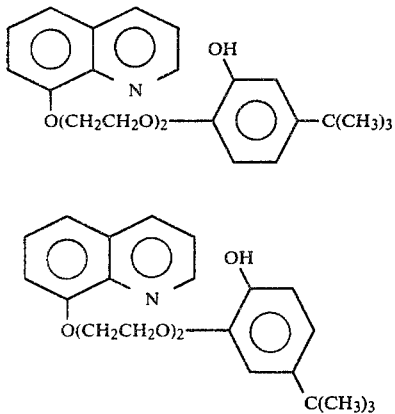

To a mixture containing 2.5 g of the above product and 0.16 g of sodium hydride in 30 ml of dimethylformamide was added 1.8 g of an ester of the formula:

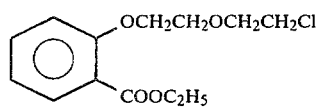

and the resulting mixture was allowed to react at 70° C. for 5 days with stirring. The reaction mixture was then added with water and solvent extraction was performed with 100 ml benzene. The benzene layer was washed with water and dried over magnesium sulfate. Thereafter, benzene was distilled off and the residue was subjected to column chromatography, thereby to obtain 2.5 g of ester compounds. The hydrolysis with alkali and purification gave a product consisting of the following polyether compounds in equal proportion. Elementary analysis of the product showed C: 69.91, H: 6.23 and N: 2.54 (theoretical value: C: 69.25, H: 6.67 and N: 2.38). The structure of the polyether product was ellusidated from IR, NMR and Mass spectra.

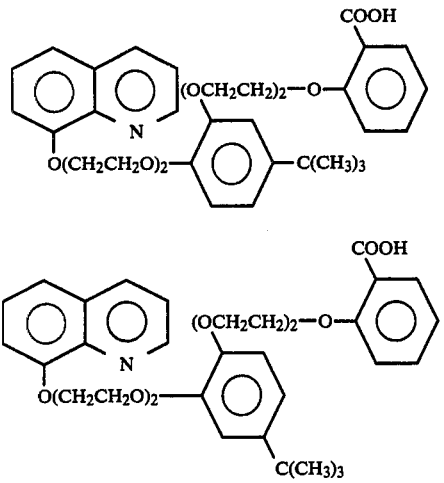

EXAMPLE 2

To a mixture of 3.5 g (0.032 mol) of pyrocatechine and 0.4 g (0.016 mol) of sodium hydride in 30 ml of dimethylformamide were added 4.1 g (0.016 mol) of the following quinoline derivative and the mixture was allowed to react at 70° C. for 2 days with stirring.

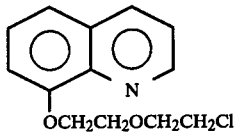

After completion of the reaction, the reaction mixture was added with water. Solvent extraction was performed twice with chloroform and the chloroform layer was, after being washed with water, dried over magnesium sulfate. Thereafter, chloroform was distilled off and the residue was subjected to column chromatography, thereby to separate 3.50 g of the following compound.

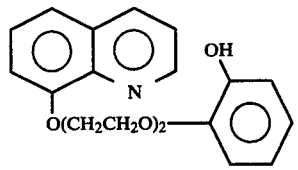

To a mixture containing 3.25 g of the thus obtained compound and 0.24 g of sodium hydride in 50 ml of dimethylformamide were added 3.5 g of the following ester and the resulting mixture was allowed to react at 70° C. for 5 days with stirring.

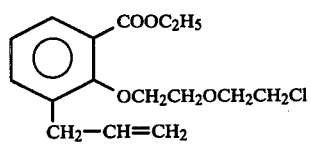

The reaction mixture was then treated in the same manner as that in Example 1, thereby to obtain 3.9 g of a polyether having the following formula.

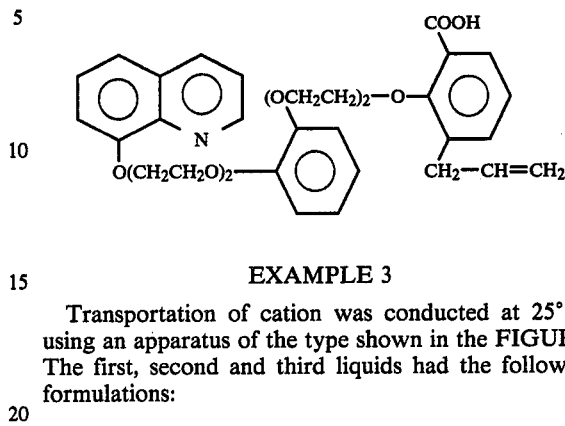

EXAMPLE 3

Transportation of cation was conducted at 25° C. using an apparatus of the type shown in the FIGURE. The first, second and third liquids had the following formulations:

| First liquid: | |
|---|---|
| 0.1 N aqueous MOH solution | 15 ml |
| Second liquid: | |
| 0.2 N aqueous MCl solution | 7.5 ml |
| 0.2 N HCl | 7.5 ml |
| Third liquid: | |
| Chloroform | 30 ml |
| Mixed polyether product obtained in Example 1 | $1.5 \times 10^{-4}$ mols |

The amount of the cation M transported from the first liquid to the second liquid with the lapse of time was as shown in Table 1.

TABLE 1

| Experiment No. | Cation M | Amount of cation M transported (%)* | | |
|---|---|---|---|---|
| | | 1 day | 2 days | 3 days |
| 1 | Li | 32 | 48 | 50 |
| 2 | Na | 38 | 49 | 50 |
| 3 | K | 46 | 50 | 50 |
| 4 | Rb | 40 | 50 | 50 |
| 5 | Cs | 39 | 49 | 50 |

*Amount of cation M transported (%) = $\dfrac{\text{Amount of cation M increased in the second liquid}}{\text{Amount of cation M originally present in the first liquid}} \times 100 \, (\%)$

EXAMPLE 4

Transportation of cations was performed in the same manner as that in Example 3 except that the following liquids were used as the first and second liquids:

| First liquid: | |
|---|---|
| 0.3 N aqueous LiOH solution | 5 ml |
| 0.3 N aqueous NaCl solution | 5 ml |
| 0.3 N aqueous KCl solution | 5 ml |
| Second liquid | |
| 0.4 N aqueous LiCl solution | 3.75 ml |
| 0.4 N aqueous NaCl solution | 3.75 ml |
| 0.4 N aqueous KCl solution | 3.75 ml |
| 0.4 N HCl | 3.75 ml |

The amount of each cation transported was as shown in Table 2.

TABLE 2

| Cation M | Amount of cation M transported (%) | |
|---|---|---|
| | 1 day | 2 days |
| Li | 0 | 0 |

TABLE 2-continued

| Cation M | Amount of cation M transported (%) | |
|---|---|---|
| | 1 day | 2 days |
| Na | 6 | 9 |
| K | 29 | 40 |

EXAMPLE 5

Example 4 was repeated using the following solutions as the first and second liquids:

| First liquid: | |
|---|---|
| 0.3 N aqueous NaOH solution | 5 ml |
| 0.3 N aqueous KCl solution | 5 ml |
| 0.3 N aqueous CsCl solution | 5 ml |
| Second liquid: | |
| 0.4 N aqueous NaCl solution | 3.75 ml |
| 0.4 N aqueous KCl solution | 3.75 ml |
| 0 4 N aqueous CsCl solution | 3.75 ml |
| 0.4 N HCl | 3.75 ml |

The amount of each cation transported was shown in Table 3.

TABLE 3

| Cation M | Amount of cation M transported (%) | |
|---|---|---|
| | 1 day | 2 days |
| Na | 4 | 6 |
| K | 27 | 36 |
| Cs | 6 | 8 |

EXAMPLE 6

Example 4 was repeated using the following solutions as the first and second liquids.

| First liquid: | |
|---|---|
| 0.2 N aqueous KOH solution | 7.5 ml |
| 0.2 N aqueous RbCl solution | 7.5 ml |
| Second liquid: | |
| 0.3 N aqueous KCl solution | 5 ml |
| 0.3 N aqueous RbCl solution | 5 ml |
| 0.3 N HCl | 5 ml |

The amount of each cation transported was as shown in Table 4.

TABLE 4

| Cation M | Amount of cation M transported (%) | |
|---|---|---|
| | 1 day | 2 days |
| K | 24 | 34 |
| Rb | 12 | 17 |

I claim:

1. A polyether having the following general formula:

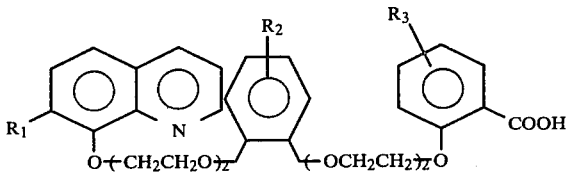

wherein $R_1$, $R_2$ and $R_3$ each stand for hydrogen, a tert-butyl group or an allyl group, with the exception that $R_1$, $R_2$ and $R_3$ cannot stand for hydrogen at the same time.

2. A polyether having the formula:

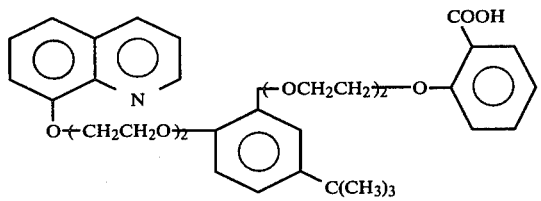

3. A polyether having the formula:

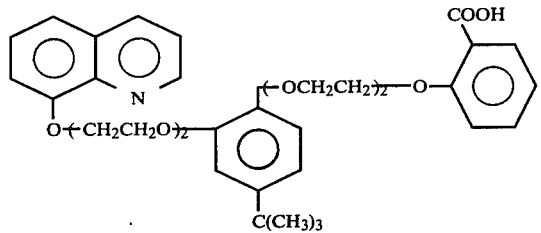

4. A polyether having the formula:

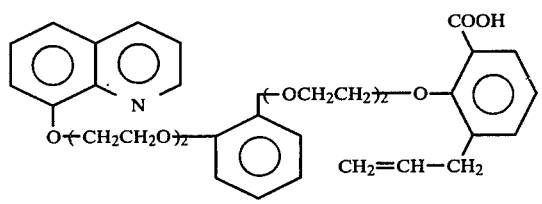

* * * * *